Sept. 3, 1946. A. R. GOLDSBY Re 22,786
MANUFACTURE OF HIGH ANTIKNOCK HYDROCARBONS
Original Filed Feb. 10, 1940
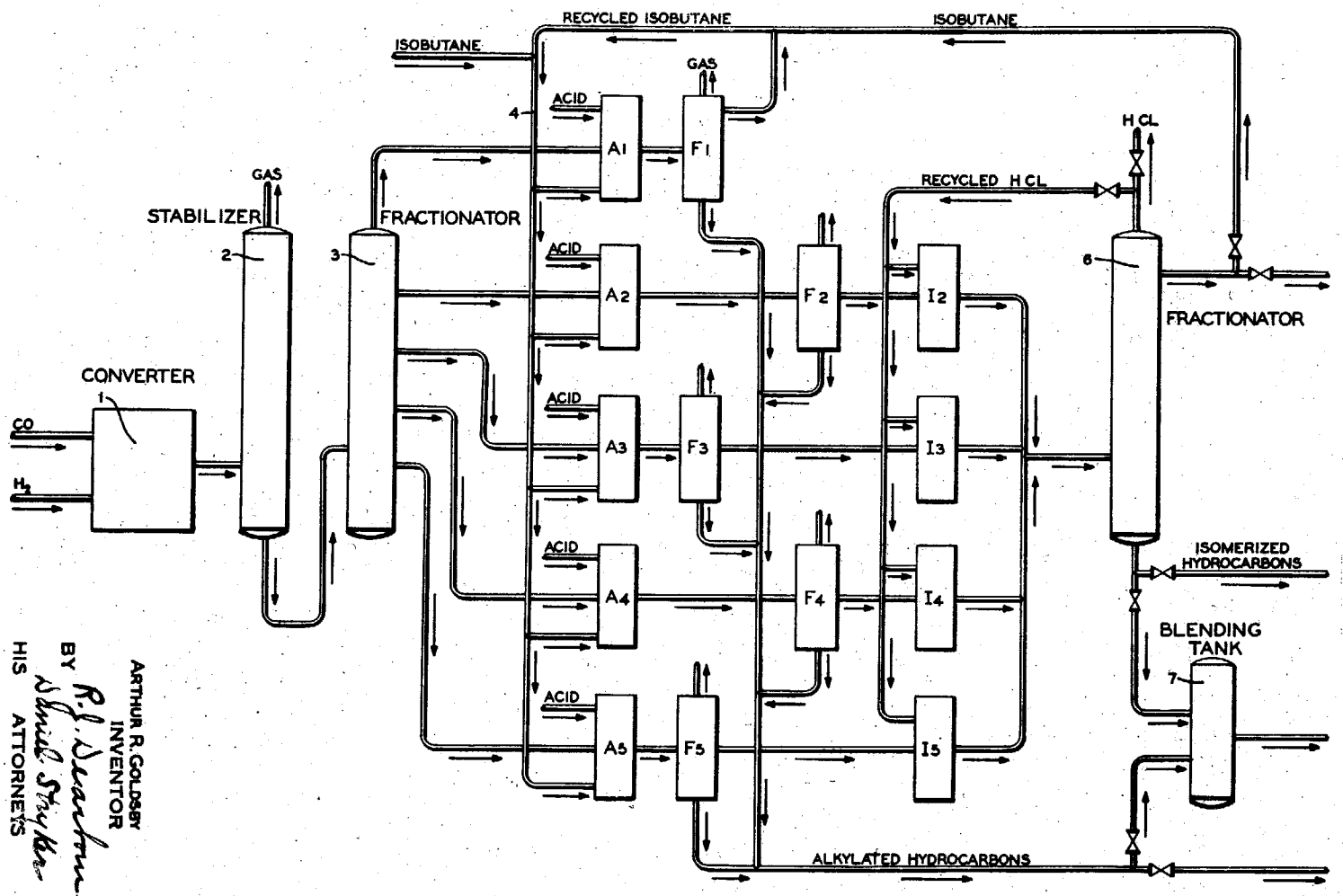
ARTHUR R. GOLDSBY
INVENTOR
BY R. J. Dearborn
Daniel Stryker
HIS ATTORNEYS Reissued Sept. 3, 1946

Re. 22,786

UNITED STATES PATENT OFFICE 22,786

MANUFACTURE OF HIGH ANTIKNOCK HYDROCARBONS

Arthur R. Goldsby, Beacon, N. Y., assignor, by mesne assignments, to The Texas Company, New York, N. Y., a corporation of Delaware Original No. 2,303,735, dated December 1, 1942, Serial No. 318,219, February 10, 1940. Application for reissue May 14, 1943, Serial No. 487,037

13 Claims. (Cl. 260—683.4)

This invention relates to a process of manufacturing high anti-knock hydrocarbons suitable for motor fuel.

The invention contemplates the treatment of cracked or synthetic hydrocarbon mixtures containing mainly normal olefin and paraffin hydrocarbons by alkylation and isomerization in a manner such as to obtain material improvement in the anti-knock characteristics of the hydrocarbon constituents.

The invention also contemplates a process in which the hydrocarbon mixture to be treated is separated into individual fractions of comparatively narrow boiling range and each fraction separately subjected to alkylation.

In accordance with the invention a hydrocarbon mixture, containing a large proportion of straight chain hydrocarbons boiling over a substantial range of temperature such as derived from the catalytic dehydrogenation of naphtha, or obtained by the catalytic conversion of carbon monoxide and hydrogen, or in some instances obtained from the thermal conversion of petroleum hydrocarbons, is fractionated into fractions of relatively narrow boiling range. Each fraction is subjected to alkylation with an isoparaffin hydrocarbon, preferably isobutane, and the alkylated fractions are, in turn, subjected to some further treatment as may be desired.

According to one method of disposition these alkylated fractions are fractionated to remove therefrom an intermediate fraction corresponding approximately in boiling range to the initial fraction from which it was derived. The resulting intermediate fractions, comprising mainly normal paraffin hydrocarbons, are then subjected to isomerization to produce isoparaffins. Isobutane formed in the isomerization is advantageously separated and recycled to the alkylation stage or stages, and the remaining isomerized hydrocarbons are blended with alkylated hydrocarbons to produce motor fuel of desired boiling range.

Instead of subjecting the intermediate fractions to isomerization they may be subjected to other forms of treatment, such as dehydrogenation, cyclization, etc., to produce products of desired characteristics.

An important object of the invention, however, is to segregate hydrocarbon constituents of a feed mixture, such as described above, and to separately alkylate the segregated hydrocarbons rather than the composite mixture.

By separately alkylating narrow cuts of the feed mixture, rather than the entire mixture, it is possible to obtain hydrocarbon mixtures containing alkylated hydrocarbons which can be fractionally separated into a fraction consisting essentially of unreacted normal paraffin hydrocarbons present in the charge, and a fraction or fractions consisting essentially of alkylated hydrocarbons of either lower or higher boiling range than the unreacted hydrocarbons.

Alkylating a wide cut containing hydrocarbons boiling over a substantial range of temperature results in the formation of a reaction mixture containing alkylated hydrocarbons coextensive in boiling temperature range with normal paraffin hydrocarbons ordinarily present in the feed. Due to this similarity in boiling temperature the normal paraffins and alkylated olefins, therefore, cannot be completely separated from each other by fractional distillation. In other words, it is impossible by means of fractional distillation to segregate the alkylated hydrocarbons into fractions containing a relatively small proportion of normal paraffins, the presence of which in large proportion may be undesired, due to their low anti-knock value.

The present invention affords a means of segregating the alkylated hydrocarbons resulting from a change mixture of the type in question so as to produce hydrocarbon fractions containing a high concentration of hydrocarbons having a high anti-knock value.

The invention has particular application to the treatment of synthetic hydrocarbon mixtures such as mentioned above and which are composed largely of normal paraffins and normal olefins ranging from normally gaseous hydrocarbons to liquid hydrocarbons boiling up to 350–400° F. and even higher. It has been found that straight-chain olefins have more of a tendency than the branch-chain olefins to build up into higher molecular weight compounds during the alkylation reaction. For example, a higher boiling range product is obtained from the alkylation of normal amylene than from the alkylation of isoamylene.

In other words, when alkylating a feed consisting essentially of branched chain liquid olefins, the resulting alkylate has a boiling range substantially coextensive with that of the feed, whereas when the feed consists largely of straight chain olefins the resulting alkylate has a boiling range which is materially wider than that of the feed. In the latter case, the alkylate will include hydrocarbons boiling both below and above the boiling temperature range of the feed hydrocarbons, the higher boiling hydrocarbons usually predominating.

Thus, where the feed mixture consists mainly of straight-chain hydrocarbons, alkylation of narrow cuts of the feed will produce products consisting essentially of compounds boiling above the end boiling points of the respective cuts from which produced. Therefore, that portion of the hydrocarbon mixture issuing from such an alkylation operation and which has a boiling range corresponding substantially to the boiling range of the particular cut being charged to that alkylation operation, will comprise mainly normal paraffin hydrocarbons which can be readily removed from the alkylate by fractionation and subjected to other forms of treatment.

Normal paraffin material so obtained in this way from the synthetic feed in question is particularly suitable for isomerization since it is essentially free from aromatic and naphthenic constituents.

Moreover, alkylation prior to isomerization has the further advantage of removing substances, such as diolefins, hydrogen sulphide and amines, from the feed and which substances are injurious to the isomerization catalyst.

Reference will now be made to the accompanying drawing showing a flow diagram illustrating one method of practicing the process of the invention.

Carbon monoxide and hydrogen, or a gaseous mixture thereof, in suitable proportions are passed to a catalytic converter 1 wherein the gaseous mixture is brought into contact with a conversion catalyst to effect conversion into hydrocarbons having a substantial olefin content.

The catalyst may comprise metals such as cobalt, nickel, iron, manganese or the oxides thereof, with or without a promoter such as thorium oxide. The catalyst is advantageously supported upon a material such as diatomaceous earth. Nickel, for example, is a preferred catalyst from the standpoint of increasing the olefin production relative to the production of saturated hydrocarbons.

The carbon monoxide and hydrogen may be charged to the converter in the ratio of around one mol of carbon monoxide to about two mols of hydrogen. By decreasing somewhat the ratio of hydrogen to carbon monoxide it is possible to increase the yield of olefins produced.

The temperature maintained within the converter may range from around 330 to 400° F. and the reaction may be carried out under a pressure of about atmospheric, although somewhat higher pressures may be employed up to about ten atmospheres, for example.

Instead of a single converter the reaction may be carried out in stages, using two or more converters in series. The products of conversion comprise normally gaseous and normally liquid hydrocarbons composed of around 60 to 70% by weight of hydrocarbons containing from one to about ten carbon atoms, with the remainder comprising higher boiling hydrocarbons.

The hydrocarbon products of reaction, including unreacted carbon monoxide and hydrogen, are passed to a stabilizer 2 wherein the unreacted materials, hydrogen and carbon monoxide, are removed in the form of a gas and which may be recycled ultimately to the converter 1. Where there is an appreciable quantity of methane, ethane and ethylene present it may be desirable to remove these constituents from the conversion products.

The liquid accumulating in the bottom of the stabilizer 2 is conducted to a fractionator 3 wherein the synthetic hydrocarbon mixture is separated into a plurality of fractions. The normally gaseous hydrocarbon fraction, amounting to about 8 or 10% of the mixture, is removed in vapor form from the top of the fractionator. This fraction will contain hydrocarbons, such as propane, butane, propylene and butylene, and the olefin content may be around 50 to 55% by volume.

This gaseous fraction is conducted to an alkylation unit $A_1$ wherein it is treated, in the presence of concentrated sulphuric acid, with isobutane from a pipe 4. It is desirable to use an acid having a concentration of around 90 to 100% and, preferably, about 94 to 98% $H_2SO_4$. The temperature of alkylation may range from around 0 to 90° F., but advantageously is about 60° F. Sufficient pressure is employed to maintain the reacting materials in the liquid phase.

Also, the ratio of isobutane to olefins in the charge entering the alkylation reactor is at least about 1:1 and preferably about 3:1 to 5:1. The ratio of acid to total hydrocarbons in the reactor may be around 0.5 to 2.0 parts by volume of acid to one of hydrocarbon.

The alkylated hydrocarbons after neutralizing with an alkali solution are conducted to a fractionating unit $F_1$ wherein they are stabilized to remove normally gaseous constituents. A side stream comprising isobutane may be removed and recycled to the alkylation unit through pipe 4 previously referred to. The remaining alkylated material comprising high anti-knock hydrocarbons is drawn off and separately disposed of or blended with products subsequently produced in the process, as will be described later.

The remaining fractions removed from the fractionator 3 comprise normally liquid fractions removed as side streams and which are drawn off to separate alkylation units $A_2$, $A_3$, $A_4$, and $A_5$, respectively.

The fraction passing to the alkylation unit $A_2$ advantageously comprises hydrocarbons boiling within the range 80 to 150° F.; that passing to the unit $A_3$ will comprise hydrocarbons boiling within the range 150 to 200° F.; that passing to the unit $A_4$ will comprise hydrocarbons boiling within the range 200 to 250° F., while that passing to the unit $A_5$ will comprise hydrocarbons boiling within the range 250 to 300° F. Additional higher boiling fractions may be produced, if desired, and likewise subjected to separate alkylation.

It is also contemplated that the boiling range of the fractions may vary somewhat from the foregoing, but usually each fraction will have an end boiling temperature not more than about 25 to 75° F. above its initial boiling temperature.

In each of the alkylation units the separate fractions are subjected to alkylation with isobutane, as described above in connection with alkylation unit $A_1$.

The alkylated hydrocarbon mixtures after neutralization and upon issuing from the alkylation units are subjected to fractionation. For example, the reaction mixture from unit $A_3$ is passed to a fractionator $F_3$ wherein it may be separated into three fractions, namely, a low-boiling fraction, an intermediate fraction boiling in the range 150 to 200° F. and a higher boiling fraction boiling in the range 200 to 400° F. The intermediate fraction thus corresponds in boiling range to the fraction initially passing to the alkylation unit $A_3$. This intermediate fraction will be rich in normal paraffin hydrocarbons and is passed to an isomerization unit $I_3$ wherein it is subjected to isomerization in the presence of an isomerization catalyst such as aluminum chloride under conditions of temperature and pressure adapted to convert the normal paraffin constituents to corresponding isoparaffins. For example, this fraction may be subjected to contact with anhydrous aluminum chloride in the presence of a small amount of hydrogen halide in either the liquid or vapor phase at a temperature of about 200° F.

The higher boiling fraction as well as the lower boiling fraction produced in the fractionation unit $F_3$ will comprise alkylated hydrocarbons which may be separately disposed of or may be blended with the alkylated hydrocarbons produced in preceding or succeeding stages. In some instances it may be desirable to recycle the lower boiling fractions to the alkylation units for retreatment with the alkylation catalyst in the presence of the isoparaffin hydrocarbon.

Similarly, the remaining feed fractions produced in the fractionator 3 and alkylated in the alkylation units $A_2$, $A_4$ and $A_5$ are passed to corresponding fractionating units $F_2$, $F_4$ and $F_5$ wherein they are subjected to fractionation to separate intermediate fractions corresponding in boiling range approximately to that of the initial feed fraction.

The resulting intermediate fractions are likewise passed to isomerization units $I_2$, $I_4$ and $I_5$ wherein the paraffin fractions are subjected to isomerization.

The temperatures and other operating conditions are maintained in each isomerization unit suitable for the conversion of the paraffins undergoing treatment therein.

The products of isomerization from each isomerization unit $I_2$ to $I_5$, inclusive, are advantageously conducted to fractionating unit 6. Substantial amounts of isobutane as well as hydrogen chloride may be present and these are separated in the fractionator 6 and may be recycled to the alkylation units and isomerization units respectively for reuse.

The remaining higher boiling isoparaffins produced in the fractionator 6 are drawn off and may be blended, all or in part, in a blending tank 7, with the products of alkylation withdrawn from the fractionators $F_1$ to $F_5$, inclusive.

It is, of course, contemplated that the products obtained at different stages in the process may be separately accumulated and disposed of for producing products having special characteristics such as safety fuel and aviation gasoline, for example.

Obviously many modifications and variations of the invention, as hereinbefore set forth, may be made without departing from the spirit and scope thereof, and therefore only such limitations should be imposed as are indicated in the appended claims.

I claim:

1. In the manufacture of motor fuel of relatively high anti-knock value from a broad boiling range gasoline fraction of comparatively low anti-knock value containing substantial proportions of normally liquid olefin and straight chain paraffin hydrocarbons, the method which comprises fractionating the said broad boiling range gasoline fraction to separate the same into a plurality of normally liquid cuts, each having a relatively narrow boiling range and each containing a substantial proportion of normally liquid olefin and straight chain paraffin hydrocarbons, separately alkylating each of a plurality of said cuts with a low-boiling isoparaffin boiling below the boiling range of the respective cut in the presence of an alkylation catalyst under alkylating conditions, whereby the isoparaffin is alkylated by the olefin of said cut to produce alkylated hydrocarbons of relatively high anti-knock value boiling largely above the boiling range of said charge cut, separately fractionating the hydrocarbon reaction products from each said alkylation reaction to separate the same into a higher boiling alkylate, lower boiling products, and a fraction of intermediate boiling range approximating the boiling range of the respective charge cut and containing mainly unreacted straight chain paraffin hydrocarbons and being essentially free from aromatic hydrocarbons, catalytically isomerizing in the presence of an isomerization catalyst a plurality of said intermediate boiling range fractions obtained from the separate fractionation of the reaction products of said plurality of alkylation reactions to thereby convert straight chain paraffins to branch chain paraffins of gasoline boiling range, and blending said plurality of alkylates and branch chain paraffins of gasoline boiling range from said isomerization to thereby produce motor fuel hydrocarbons of relatively high anti-knock value.

2. The method according to claim 1, wherein the said low-boiling isoparaffin employed for the said alkylation reactions is isobutane.

3. The method according to claim 1, wherein the isomerization of said intermediate boiling range fractions results in the production of isobutane in addition to branch chain paraffins of gasoline boiling range, and at least a portion of said isobutane produced in the isomerization reaction is recycled to at least one of said alkylation reactions.

4. The method according to claim 1, in which at least a portion of the said low-boiling products separated in the fractionation of the hydrocarbon reaction products of each alkylation reaction is recycled to the respective alkylation reaction.

5. The method according to claim 1, wherein the said broad boiling range gasoline fraction is a synthetic hydrocarbon mixture obtained from the catalytic conversion of carbon monoxide and hydrogen, said mixture being composed largely of normal paraffins and normal olefins, and being essentially free from aromatic and naphthenic hydrocarbons.

6. The method of improving the anti-knock value of a narrow cut gasoline fraction of relatively low anti-knock value having an end boiling point not more than about 25 to 75° F. higher than its initial boiling point and containing substantial proportions of normally liquid olefin and straight chain paraffin hydrocarbons, which comprises reacting the said fraction with a low-boiling isoparaffin boiling below the boiling range of said fraction in the presence of an alkylation catalyst under alkylating conditions, whereby the isoparaffin is alkylated by the olefin of said fraction to produce alkylated hydrocarbons of relatively high anti-knock value boiling largely above the boiling range of said charge fraction, fractionating the hydrocarbon reaction products of said alkylation reaction to separate the same into a higher boiling alkylate, lower boiling products, and a fraction of intermediate boiling range approximating the boiling range of the said charge fraction and containing mainly unreacted straight chain paraffin hydrocarbons and being essentially free from aromatic hydrocarbons, catalytically isomerizing said fraction of intermediate boiling range in the presence of an isomerization catalyst to thereby convert straight chain paraffins to branch chain paraffins of gasoline boiling range with the concomitant production of isobutane, fractionating the products of isomerization to separate the isobutane and other normally gaseous products from a normally liquid isomerizate boiling within the gasoline boiling range, and blending the said higher boiling alkylate with the said isomerizate to thereby produce a gasoline fraction of substantially improved anti-knock value.

7. The method according to claim 6, in which the said low-boiling isoparaffin employed in the alkylation reaction is isobutane.

8. The method according to claim 6, in which at least a portion of the isobutane produced in the isomerization reaction is recycled to the alkylation reaction.

9. The method according to claim 6, in which at least a portion of the lower boiling products separated in the fractionation of the alkylation reaction products is recycled to the alkylation reaction.

10. The method according to claim 6, wherein the said narrow cut gasoline fraction is a synthetic hydrocarbon mixture obtained from the catalytic conversion of carbon monoxide and hydrogen, said mixture being composed largely of normal paraffins and normal olefins, and being essentially free from aromatic and naphthenic hydrocarbons.

11. The method of improving the anti-knock value of a narrow cut normally liquid gasoline fraction of relatively low anti-knock value having an end boiling point not more than about 25 to 75° F. higher than its initial boiling point and containing substantial proportions of normally liquid straight chain olefin and paraffin hydrocarbons, which comprises reacting the said fraction with a low-boiling isoparaffin boiling below the boiling range of said fraction in the presence of an alkylation catalyst under alkylating conditions, whereby the isoparaffin is alkylated by the olefin of said fraction to produce alkylated hydrocarbons of relatively high anti-knock value boiling largely above the boiling range of said charge fraction, fractionating the hydrocarbon reaction products of said alkylation reaction to separate the same into a higher boiling alkylate, lower boiling products, and a fraction of intermediate boiling range approximating the boiling range of the said charge fraction and containing mainly unreacted straight chain paraffin hydrocarbons, subjecting the said intermediate boiling range fraction to a conversion treatment to produce products of higher anti-knock value, and blending at least a portion of said conversion products of higher anti-knock value with said higher boiling alkylate to produce motor fuel of high anti-knock value.

12. The method according to claim 11, wherein the said conversion treatment includes dehydrogenation.

13. The method according to claim 11, wherein the said conversion treatment includes cyclization.

ARTHUR R. GOLDSBY.